US012029720B2

(12) United States Patent
Adair et al.

(10) Patent No.: US 12,029,720 B2
(45) Date of Patent: Jul. 9, 2024

(54) CANNABIDIOL-DOMINANT FORMULATIONS, METHODS OF MANUFACTURING, AND USES THEREOF

(71) Applicant: Tilray, Inc., New York, NY (US)

(72) Inventors: Christopher Adair, Woodstock (CA); Steven Nazarian, London (CA)

(73) Assignee: TILRAY BRANDS, INC., Leamington (CA)

( * ) Notice: Subject to any disclaimer, the term of this patent is extended or adjusted under 35 U.S.C. 154(b) by 0 days.

(21) Appl. No.: 17/733,458

(22) Filed: Apr. 29, 2022

(65) Prior Publication Data

US 2022/0347152 A1 Nov. 3, 2022

Related U.S. Application Data

(60) Provisional application No. 63/181,955, filed on Apr. 29, 2021.

(51) Int. Cl.
*A61K 31/352* (2006.01)
*A61K 36/185* (2006.01)
*B01D 11/02* (2006.01)

(52) U.S. Cl.
CPC .......... *A61K 31/352* (2013.01); *A61K 36/185* (2013.01); *B01D 11/0288* (2013.01); *A61K 2236/33* (2013.01)

(58) Field of Classification Search
None
See application file for complete search history.

(56) References Cited

U.S. PATENT DOCUMENTS

| | | | |
|---|---|---|---|
| 6,730,330 B2 | 5/2004 | Whittle et al. | |
| 7,094,786 B2 | 8/2006 | Landau et al. | |
| 8,034,843 B2 | 10/2011 | Whittle et al. | |
| 8,119,697 B2 | 2/2012 | Mechoulam et al. | |
| 8,481,091 B2 | 7/2013 | Ross | |
| 8,642,080 B2 | 2/2014 | Bender et al. | |
| 8,691,272 B2 | 4/2014 | Zerbe et al. | |
| 9,308,175 B2 | 4/2016 | Pellikaan et al. | |
| 9,375,417 B2 | 6/2016 | Smith et al. | |
| 9,433,582 B2 | 9/2016 | Devarakonda et al. | |
| 9,616,025 B2 | 4/2017 | De Vries et al. | |
| 9,730,911 B2 | 8/2017 | Verzura et al. | |
| 9,895,322 B2 | 2/2018 | Singh et al. | |
| 9,907,823 B1 | 3/2018 | Kuhrts | |
| 10,004,684 B2 | 6/2018 | Whittle et al. | |
| 10,137,161 B2 | 11/2018 | Kolsky | |
| 10,179,683 B2 | 1/2019 | Whittle | |
| 10,206,901 B2 | 2/2019 | Cranford et al. | |
| 10,213,391 B2 | 2/2019 | Singh | |
| 10,238,745 B2 | 3/2019 | Finley et al. | |
| 10,245,237 B2 | 4/2019 | De Vries et al. | |
| 10,383,819 B1 | 8/2019 | Thompson et al. | |
| 10,413,845 B1 | 9/2019 | Tegen et al. | |
| 10,662,137 B2 | 5/2020 | Qu et al. | |
| 10,864,458 B2 | 12/2020 | Nadal Roura | |
| 2003/0229027 A1 | 12/2003 | Eissens et al. | |
| 2004/0138293 A1 | 7/2004 | Werner et al. | |
| 2004/0248970 A1 | 12/2004 | Webster et al. | |
| 2006/0135599 A1 | 6/2006 | Symonds et al. | |
| 2006/0167283 A1 | 7/2006 | Flockhart et al. | |
| 2007/0072939 A1 | 3/2007 | Kupper | |
| 2007/0104741 A1 | 5/2007 | Murty et al. | |
| 2008/0139667 A1 | 6/2008 | Robson et al. | |
| 2010/0286098 A1 | 11/2010 | Robson et al. | |
| 2014/0271940 A1 | 9/2014 | Wurzer | |
| 2015/0181924 A1 | 7/2015 | Llamas | |
| 2015/0374770 A1 | 12/2015 | Crowley | |
| 2016/0000843 A1 | 1/2016 | Lowe et al. | |
| 2016/0020936 A1 | 1/2016 | Hu et al. | |
| 2016/0256411 A1 | 9/2016 | Aung-Din | |
| 2016/0309774 A1 | 10/2016 | Wand | |
| 2017/0021029 A1 | 1/2017 | Raber et al. | |
| 2017/0056368 A1 | 3/2017 | Hearn et al. | |
| 2017/0348276 A1 | 12/2017 | Bryson et al. | |

(Continued)

FOREIGN PATENT DOCUMENTS

| | | |
|---|---|---|
| CA | 2995970 A1 | 8/2018 |
| CA | 3024645 A1 | 1/2019 |

(Continued)

OTHER PUBLICATIONS

American Psychiatric Association, "Diagnostic and Statistical Manual of Mental Disorders," (5th ed.), American Psychiatric Publishing, Washington, D.C., May 2013, 16 pages.
Halldin et al., "Urinary Metabolites of Delta-1-Tetrahydrocannabinol in Man," Arzneimittel-Forschung, 32(7):764-768, Jan. 1982.
Tansey et al., "The Challenges in the Development of Metered Dose Inhalation Aerosols Using Ozone-Friendly Propellants," Spray Technol. Market, 4:26-29, 1994.
Trembly et al., "Double-blind Clinical Study of Cannabidiol as a Secondary Anticonvulsant," Marijuana '90 Int'l Conference on Cannabis and Cannabinoids, Int'l Association for Cannabinoid Medicines, Jul. 8-11, 1990, Abstract only.
International Patent Application No. PCT/US2022/027027, International Search Report and Written Opinion mailed Jul. 19, 2022, 13 pages.

(Continued)

*Primary Examiner* — Michael V Meller
(74) *Attorney, Agent, or Firm* — Fredrikson & Byron, P.A.

(57) ABSTRACT

Stable liquid formulations dominant in cannabidiol (CBD) can be manufactured by a sequential process of purification to create a formulation that does not crystallize under a variety of storage and use conditions, and without the use of potentially harmful additives. For example, the formulation may be used in vaporization devices (i.e., electronic cigarettes) that typically require formulations to remain in a non-crystalline, non-solid, or non-partially solid state. The liquid formulations dominant in CBD may further contain other phytocannabinoids, including, but not limited to, tetrahydrocannabinol (THC), cannabigerol (CBG), cannabichromene (CBC), cannabinol (CBN), and cannabidivarin (CBDV) in higher concentrations than unrefined and refined *cannabis* extracts obtained via existing methods.

8 Claims, 3 Drawing Sheets

(56) References Cited

U.S. PATENT DOCUMENTS

| | | |
|---|---|---|
| 2018/0020699 A1 | 1/2018 | Steup |
| 2018/0042845 A1 | 2/2018 | Sinai et al. |
| 2018/0042975 A1 | 2/2018 | Ford et al. |
| 2018/0085308 A1 | 3/2018 | Renwick et al. |
| 2018/0116998 A1 | 5/2018 | Sinai et al. |
| 2018/0207213 A1 | 7/2018 | Mcelvany |
| 2018/0264121 A1 | 9/2018 | Donaduzzi et al. |
| 2018/0289062 A1 | 10/2018 | Lopez |
| 2018/0289665 A1 | 10/2018 | Turner et al. |
| 2018/0303791 A1 | 10/2018 | Sinai et al. |
| 2019/0010107 A1 | 1/2019 | Oroskar et al. |
| 2019/0015381 A1 | 1/2019 | Fanous |
| 2019/0015382 A1 | 1/2019 | Davidson et al. |
| 2019/0022054 A1 | 1/2019 | Greenbaum et al. |
| 2019/0022055 A1 | 1/2019 | Siegel et al. |
| 2019/0060300 A1 | 2/2019 | Anavi-Goffer |
| 2019/0110981 A1 | 4/2019 | Weimann |
| 2019/0134121 A1 | 5/2019 | Bermudez et al. |
| 2019/0134122 A1 | 5/2019 | Pertile |
| 2019/0224118 A1 | 7/2019 | Navon et al. |
| 2020/0037638 A1 | 2/2020 | Faraci et al. |
| 2020/0297025 A1 | 9/2020 | Alsayar et al. |
| 2020/0338038 A1 | 10/2020 | Malcolm |

FOREIGN PATENT DOCUMENTS

| | | |
|---|---|---|
| EP | 3485885 A1 | 5/2019 |
| JP | 2005512943 A | 5/2005 |
| MX | PA05001567 A | 4/2005 |
| WO | 2006124698 A2 | 11/2006 |
| WO | 2015193667 A1 | 12/2015 |
| WO | 2015193668 A1 | 12/2015 |
| WO | 2016059403 A1 | 4/2016 |
| WO | 2016094810 A2 | 6/2016 |
| WO | 2016189384 A1 | 12/2016 |
| WO | 2017137992 A1 | 8/2017 |
| WO | 2017193169 A1 | 11/2017 |
| WO | 2017203529 A1 | 11/2017 |
| WO | 2018002636 A1 | 1/2018 |
| WO | 2018011808 A1 | 1/2018 |
| WO | 2018044953 A1 | 3/2018 |
| WO | 2018061007 A1 | 4/2018 |
| WO | 2018071581 A1 | 4/2018 |
| WO | 2018085794 A1 | 5/2018 |
| WO | 2018115962 A1 | 6/2018 |
| WO | 2018152334 A1 | 8/2018 |
| WO | 2018183151 A1 | 10/2018 |
| WO | 2019056128 A1 | 3/2019 |
| WO | 2019100007 A1 | 5/2019 |
| WO | 2019135224 A1 | 7/2019 |
| WO | 2019135225 A1 | 7/2019 |
| WO | 2019159176 A1 | 8/2019 |
| WO | 2019161231 A1 | 8/2019 |
| WO | 2019165387 A1 | 8/2019 |
| WO | 2020212971 A1 | 10/2020 |
| WO | 2021154719 A1 | 8/2021 |

OTHER PUBLICATIONS

Gonda, I. "Aerosols for Delivery of Therapeutic and Diagnostic Agents to the Respiratory Tract," In: Critical Reviews in Therapeutic Drug Carrier Systems, 1990, 6:273-313.

Grinspoon et al., "Marihuana, the Forbidden Medicine," New Haven: Yale University Press, 1993, pp. 58-67.

Harvey et al., "Metabolites of Cannabidiol Identified in Human Urine," Xenobiotica, 20(3):303-320, Mar. 1990.

Health Canada, "Information for Health Care Professionals: Cannabis (Marihuana, Marijuana) and the Cannabinoids," Spring 2018, 158 pgs.

Hirsch L, Donner E, So E et al. "Abbreviated report of the NIH/NINOS workshop on SUDEP." Neural 2011 ;76(22): 1932-38.

Huestis, M., "Human Cannabinoid Pharmacokinetics," Chem Biodivers., 4(8):1770-1804, Aug. 2007 (NIH Public Access—Author's Manuscript).

Izquierdo et al., "The Effect of Cannabidiol on Maximal Electroshock Seizures in Rats," J Pharm Pharmacol., 25(11):916-917, Nov. 1973.

Jones, N., Glyn, S., Akiyama, S., Hill, T., & Hill, A. "Cannabidiol exerts anti-convulsant effects in animal models of temporal lobe." Seizure 2012;21: 344-52.

Jones, N., Hill, A., Smith, I., Bevan, S., & Williams, C. "Cannabidiol displays antiepileptiform and antiseizure properties In vitro and in vivo." JournPharmacol ExperTherap 2010; 332(2): 569-577.

Karler, R., & Turkanis, S. "Subacute cannabinoid treatment: anticonvulsant activity and withdrawal excitability in mice." Br J Pharmacol 1980; 68(3):479-84.

Kobayashi, et al., "Pulmonary Delivery of Salmon Calcitonin Dry Powders Containing Absorption Enhancers in Rats," Pharma Res., 13(1):80-83, Feb. 1996.

Kramer, J., "Medical Marijuana for Cancer," CA Cancer J. Clin., 65(2):109-122, Mar. 2015.

Kreitzer et al., "The Therapeutic Potential of Novel Cannabinoid Receptors," Pharmacol. Ther., 122(2):83-96, May 2009 (NIH Public Access—Author's Manuscript).

Leo Antonio et al, "Cannabidiol and epilepsy: Rationale and therapeutic potential", Pharmacological Research, Academic Press, London, GB, (Mar. 11, 2016), vol. 107, doi: 10.1016/J.PHRS.2016.03.005, ISSN 1043-6618, pp. 85-92.

Maa, et al, "The case for medical marijuana in epilepsy", Epilepsia, (Jun. 1, 2014), vol. 55, No. 6, doi:10.1111/epi.12610, ISSN 0013-9580, pp. 783-786.

Mackie et al., "Cannabinoids Activate an Inwardly Rectifying Potassium Conductance and Inhibit Q-Type Calcium Currents in AtT20 Cells Transfected with Rat Brain Cannabinoid Receptor," J. Neurosci., 15(10):6552-6561, Oct. 1995.

Mackie et al., "Cannabinoids Inhibit N-type Calcium Channels in Neuroblastoma-glioma Cells," PNAS U.S.A., 89(9):3825-3829, May 1992.

Mechoulam R, Carlini EA. "Toward drugs derived from cannabis." Naturwissenschaften 1978;65:pp. 174-179.

Mersiades, Antony J, et al. "Oral cannabinoid-rich THC/CBD cannabis extract for secondary prevention of chemotherapy-induced nausea and vomiting: a study protocol for a pilot and definitive randomised double-blind placebo-controlled trial (CannabisCINV)", BMJ Open, vol. 8, No. 9, Sep. 1, 2018, 8 pgs.

Miller et al., CB2 Receptor-mediated Migration of Immune Cells: It Can Go Either Way, Br J Pharmacol., 153(2):299-308, Jan. 2008.

Nadulski et al., "Simultaneous and Sensitive Analysis of THC, 11-OH-THC, THC-COOH, CBD, and CBN by GC-MS in Plasma after Oral Application of Small Doses of THC and Cannabis Extract," J Anal Toxicol., 29(8):782-789, Nov.-Dec. 2005.

Niven et al., "The Pulmonary Absorption of Aerosolized and Intratracheally Instilled rhG-CSF and monoPEGylated rhG-CSF," Pharma Res., 12(9):1343-1349, Sep. 1995.

Novotna et al., "A Randomized, Double-Blind, Placebo-Controlled, Parallel-group, Enriched-design Study of Nabiximols* (Sativex®), as Add-on Therapy, in Subjects with Refractory Spasticity Caused by Multiple Sclerosis," Eur J Neurol., 18(9):1122-1131, Sep. 2011.

Nsativex®, Product Monograph, GW Pharma Ltd., pp. 1-55, Mar. 2015.

Pacher et al., "The Endocannabinoid System as an Emerging Target of Pharmacotherapy," Pharmacol Rev., 58(3):389-462, Sep. 2006.

Pack, A.M., "SUDEP: What Are the Risk Factors? Do Seizures or Antiepileptic Drugs Contribute to an Increased Risk?," Epilepsy Curr., 12(4): 131-132, Jul.-Aug. 2012.

Patton et al., "(D) Routes of delivery: Case studies: (2) Pulmonary Delivery of Peptides and Proteins for Systemic Action," Adv Drug Deliv Rev., 8(2-3):179-196, Mar.-Jun. 1992.

Patton et al., "Bioavailability of Pulmonary Delivered Peptides and Proteins: A-Interferon, Calcitonins and Parathyroid Hormones," Advances in Drug Delivery Systems, 6, Proc.of the Sixth Int'l Symposium on Recent Advances in Drug Delivery Systems, pp. 79-85, Feb. 1993.

(56) References Cited

OTHER PUBLICATIONS

Pertwee, R., "Receptors and Channels Targeted by Synthetic Cannabinoid Receptor Agonists and Antagonists," Curr Med Chem., 17(14):1360-1381, Jan. 2011.
Pertwee, Roger Guy, et al. "International Union of Basic and Clinical Pharmacology. LXXIX. Cannabinoid receptors and their ligands: beyond CB1 and CB2." Pharmacological reviews 62.4 (2010): 588-631.
Press et al., "Parental reporting of response to oral cannabis extracts for treatment of refractory epilepsy," Epilepsy & Behavior, vol. 45, Apr. 3, 2015, pp. 49-52, Abstract Only.
Richardson et al., "Validity and Reliability of the Assessment of Quality of Life (AQoL)-8D Multi-Attribute Utility Instrument," Patient, 2014;7(1):85-96, published online Nov. 2013.
Rock, Erin M., et al. "Cannabinoids as Potential Treatment for Chemotherapy-Induced Nausea and Vomiting", Frontiers in Pharmacology, vol. 7, Jul. 26, 2016, 10 pgs.
Rock Erin M et al: "Synergy between cannabidiol, cannabidiolic acid, and [Delta] 9-tetrahydrocannabinol in the regulation of emesis in the *Suncus murinus* (house musk shrew).", Behavioral Neuroscience, vol. 129, No. 3, 2015, pp. 368-370.
Roila et al., "Guideline Update for MASCC and ESMO in the Prevention of Chemotherapy- and Radiotherapy-induced Nausea and Vomiting: Results of the Perugia Consensus Conference," Ann Oncol., 21(Suppl 5):v232-243, May 2010.
Ross et al., "Inhibition of Recombinant Human T-type Calcium Channels by Δ 9-Tetrahydrocannabinol and Cannabidiol*," J Biol Chem., 283(23):16124-16134, Jun. 2008.
Rudt et al., "In Vitro Phagocytosis Assay of Nano- and Microparticles by Chemiluminescence. I. Effect of Analytical Parameters, Particle Size and Particle Concentration," J Controlled Release, 22(3):263-271, Nov. 1992.
Russo E., "History of Cannabis and Its Preparations in Saga, Science, and Sobriquet," Chem Biodivers., 4(8):1614-1648, Aug. 2007.
Russo et al., "Agonistic Properties of Cannabidiol at 5-HT1a Receptors," Neurochem Res., 30(8):1037-1043, Aug. 2005.
Russo et al: "A tale of two cannabinoids: The therapeutic rationale for combining tetrahydrocannabinol and cannabidiol", Medical Hypotheses, vol. 66, No. 2, 2006, pp. 234-246.
Ryan et al., "Cannabidiol Targets Mitochondria to Regulate Intracellular Ca2+ Levels," J Neurosci., 29(7):2053-2063, Feb. 2009.
Ryberg et al., "The Orphan Receptor GPR55 is a Novel Cannabinoid Receptor," Br J Pharmacol., 152(7):1092-1101, Dec. 2007.
Sakauchi et al., "Retrospective Multiinstitutional Study of the Prevalence of Early Death in Dravet Syndrome," Epilepsia, 52(6):1144-1149, Jun. 2011.
Serrano et al., "Endocannabinoid Influence in Drug Reinforcement, Dependence and Addiction-Related Behaviors," Pharmacol Ther., 132(3):215-241, Dec. 2011 (NIH Public Access—Author's Manuscript).
Shoemaker et al., "Agonist-Directed Trafficking of Response by Endocannabinoids Acting at CB2 Receptors," J Pharmacol Exp Ther., 315(2):828-838, Nov. 2005.
Sirven Joseph I Ed—Kasteleijn-Nolst Trenité Dorothée et al, "Medical marijuana for epilepsy: Winds of change", Epilepsy and Behavior, (Sep. 1, 2013), vol. 29, No. 3, doi:10.1016/J.YEBEH.2013.09.004, ISSN 1525-5050, pp. 435-436.
Szaflarski Jerzy P et al, "Cannabis, cannabidiol, and epilepsy— From receptors to clinical resp", Epilepsy and Behavior, Academic Press, San Diego, CA, US, (Oct. 1, 2014), vol. 41, doi:10.1016/J.YEBEH.2014.08.135, ISSN 1525-5050, pp. 277-282.
Tabata et al., "Macrophage Phagocytosis of Biodegradable Microspheres Composed of L-Lactic Acid/Glycolic Acid Homo- and Copolymers," J Biomed Mater Res., 22(10):837-858, Oct. 1988.
Tellez-Zenteno JF, Dhar R, Hernandez-Ronquillo L, Wiebe S. "Long-term outcomes in epilepsy surgery: antiepileptic drugs, mortality, cognitive and psychosocial aspects." Brain 2007; 130(Pt 2):334-45.

Tilray, "Tilray Announces a Clinical Trial Partnership in Australia," Tilray News, Feb. 2016, accessed on the internet at https://www.tilray.ca/en/blog/post/tilray-announces-a-clinical-trial-partnership-in-australia/, retrieved Oct. 4, 2019, 2 pgs.
Timsina et al., "Drug Delivery to the Respiratory Tract Using Dry Powder Inhalers," Int. J. Pharm., 101(1-2):1-13, Jan. 1994.
Turkanis et al., "An Electrophysiological Analysis of the Anticonvulsant Action of Cannabidiol on Limbic Seizures in Conscious Rats," Epilepsia, 20(4):351-363, Aug. 1979.
Tzadok Michal et al, "CBD-enriched medical cannabis for intractable pediatric epilepsy the current Israeli experience", Seizure, Bailliere Tindall, London, GB, (Jan. 6, 2016), vol. 35, doi: 10.1016/J.SEIZURE.2016.01.04, ISSN 1059-1311, pp. 41-44.
Vandrey et al., "Pharmacotherapy for Cannabis Dependence: How Close Are We?," CNS Drugs, 23(7):543-553, Jan. 2010 (NIH Public Access—Author's Manuscript).
Visser et al., "Van der Waals and Other Cohesive Forces Affecting Powder Fluidization," Powder Technol., 58(1):1-10, May 1989.
Wall, D.A., "Pulmonary Absorption of Peptides and Proteins," Drug Delivery, 2(1):1-20, 1995.
Yakoub et al, "Early Diagnosis of Severe Myoclonic Epilepsy in Infancy," Brain Dev., 14(5):299-303, Sep. 1992.
Zanen, et al., "The Optimal Particle Size for Parasympathicolytic Aerosols in Mild Asthmatics," Int J Pharma., 114(1):111-115, Jan. 1995.
Zuardi AW, Hallak JE, Dursun SM et al. "Cannabidiol monotherapy for treatment-resistant schizophrenia." J Psychopharmacol 2006;20(4):683-6.
Zuardi AW, Morais SI, Guimaraes FS, Mechoulam R. "Antipsychotic effect of cannabidiol." J Clin Psychi 1995;56 10:485-6.
Zuardi et al., "Action of Cannabidiol on the Anxiety and Other Effects Produced by Δ 9-THC in Normal Subjects," Psychopharmacology (Berl)., 76(3):245-250, Feb. 1982.
Zuardi et al., "Cannabidiol was Ineffective for Manic Episode of Bipolar Affective Disorder," J Psychopharmacol. 24 (1):135-137, Jan. 2010.
GW Pharma "Developing Novel Prescription Medicines Which Make a Real Difference to Patients' Lives," Annual Report 2015 Highlights, Dec. 2015, 335 pgs.
Aapro et al., "The Effect of Guideline-consistent Antiemetic Therapy on Chemotherapy-induced Nausea and Vomiting (CINV): The Pan European Emesis Registry (PEER)," Ann Oncol., 23(8):1986-1992, Aug. 2012.
AbbVie Inc. Marinol—Product Label Aug. 2015, 17 pgs.
Adjei et al., "Pulmonary Delivery of Peptide Drugs: Effect of Particle Size on Bioavailability of Leuprolide Acetate in Healthy Male Volunteers," Pharm Res., 7(6):565-569, Jun. 1990.
Agurell et al., "Pharmacokinetics and Metabolism of Δ1-tetrahydrocannabinol and Other Cannabinoids with Emphasis on Man," Pharmacol Rev., 38(1):21-43, Mar. 1986.
Akiyama M, Kobayashi K, Yoshinaga H, Yoshinga H, Ohtsuka Y. "A long-term follow-up study of Dravet syndrome into adulthood." Epilepsia 2010;51 :1043-52.
Allsop et al., "Nabiximols as an Agonist Replacement Therapy During Cannabis Withdrawal," JAMA Psychiatry, 71(3):281-291, Mar. 2014.
Allsop et al., "The Cannabis Withdrawal Scale Development: Patterns and Predictors of Cannabis Withdrawal and Distress," Drug Alcohol Depend., 119(1-2):123-129, Dec. 2011.
Ames FR, Cridland S. "Anticonvulsant effect of cannabidiol." South African Medical Journal 1985;69:14.
Anderson et al., "Effect of Cystic Fibrosis on Inhaled Aerosol Boluses," Am Rev Respir Dis., 140(5):1317-1324, Nov. 1989.
Arqumosa A, Herranz JL. "Childhood epilepsy: a critical review of cost-of-illness studies." Epileptic Disord 2004;6(1):31-40.
Australian Gov., "Australian Public Assessment Report for Nabiximols," pp. 1-204, Sep. 2013.
Beghi et al., "A Review of the Costs of Managing Childhood Epilepsy," Pharmacoeconomics, 23(1):27-45, Jan. 2005.
Bhattacharyya et al., "Opposite Effects of D-9-Tetrahydrocannabinol and Cannabidiol on Human Brain Function and Psychopathology," Neuropsychopharmacology, 35(3):764-774, Feb. 2010.

(56) References Cited

OTHER PUBLICATIONS

Bohnert et al., "Positive Posttraumatic Stress Disorder Screens Among First-time Medical Cannabis Patients: Prevalence and Association with Other Substance Use," Addict Behav., 39(10):1414-1417, Oct. 2014 (NIH Public Access—Author's Manuscript).

Borges et al., "Understanding the Molecular Aspects of Tetrahydrocannabinol and Cannabidiol as Antioxidants," Molecules, 18(10):12663-12674, Oct. 2013.

Bouaboula et al., "Activation of Mitogen-activated Protein Kinases by Stimulation of the Central Cannabinoid Receptor CB1," Biochem J., 312(Pt 2):637-641, Dec. 1995.

Budney et al., "Review of the Validity and Significance of Cannabis Withdrawal Syndrome," Am J Psychiatry, 161(11):1967-1977, Nov. 2004.

Byron, P.R., "Determinants of Drug and Polypeptide Bioavailability from Aerosols Delivered to the Lung," Adv. Drug Deliv. Rev., 5(1-2):107-132, May-Aug. 1990.

Campbell et al., "Bootstrapping: Estimating Confidence Intervals for Costeffectiveness Ratios," QJM., 92(3):177-182, Mar. 1999.

Carrier et al., "Inhibition of an Equilibrative Nucleoside Transporter by Cannabidiol: A Mechanism of Cannabinoid Immunosuppression," PNAS U.S.A., 103(20):7895-7900, May 2006.

Chang et al., "A Prospective Evaluation of Delta-9-Tetrahydrocannabinol as an Antiemetic in Patients Receiving Adriamycin and Cytoxan Chemotherapy," Cancer, 47(7):1746-51, Apr. 1981.

Chesher et al., "Anticonvulsant Effects of Cannabinoids in Mice: Drug Interactions Within Cannabinoids and Cannabinoid Interactions with Phenytoin," Psychpharmacologica, 37(3):255-264, Sep. 1974.

Chesher et al., "Interaction of Δ9-tetrahydrocannabinol and Cannabidiol with Phenobarbitone in Protecting Mice from Electrically Induced Convulsions," J Pharm Pharmacol., 27(8):608-609, Aug. 1975.

Consroe et al., "Controlled Clinical Trial of Cannabidiol in Huntington's Disease," Pharmacol Biochem Behav., 40(3):701-708, Nov. 1991.

Consroe et al., "Effects of Cannabidiol on Behavioral Seizures Caused by Convulsant Drugs or Current in Mice," Eur J Pharmacol., 83(3-4):293-298, Sep. 1982.

Consroe et al., "Potential Role of Cannabinoid for Therapy of Neurological Disorders," In: Marijuana/Cannabinoids Neurobiology and Neurophysiology, Boca Raton, CRC Press, 1992, 459-524.

Consroe et al., "Assay of Plasma Cannabidiol by Capillary Gas Chromatography/Ion Trap Mass Spectroscopy Following High-Dose Repeated Daily Oral Administration in Humans," Pharmacol Biochem Behav., 40(3):517-522, Nov. 1991.

Consroe et al., "Open Label Evaluation of Cannabidiol in Dystonic Movement Disorders," Int J Neurosci., 30(4):277-282, Nov. 1986.

Crippa et al., "Cannabis and Anxiety: A Critical Review of the Evidence," Hum Psychopharmacol., 24(7):515-523, Oct. 2009.

Cunha JM, Carlini EA, Pereira AE, Ramos OL, Pimentel C, Gagliardi R, et al. "Chronic administration of cannabidiol to healthy volunteers and epileptic patients." Pharmacology 1980;21 :175-85.

Damms et al, "The Cost of Delivering Drugs Without Needles," Biotechnology (NY), 13(13):1438-1440, Dec. 1995.

De Petrocellis et al. "Effects of Cannabinoids and Cannabinoid-enriched Cannabis Extracts on TRP Channels and Endocannabinoid Metabolic Enzymes," Br J Pharmacol., 163(7):1479-1494, Aug. 2011.

De Petrocellis et al. "Plant-Derived Cannabinoids Modulate the Activity of Transient Receptor Potential Channels of Ankyrin Type-1 and Melastatin Type-8," J. Pharmacol Exp Ther., 325(3):1007-1015, Jun. 2008.

Dhopeshwarkar et al., "CB2 Cannabinoid Receptors as a Therapeutic Target—What Does the Future Hold?," Mol. Pharmacol., 86:430-437, Oct. 2014.

Dill et al., "Regulation of Adenylate Cyclase by Chronic Exposure to Cannabimimetic Drugs," J Pharmacol Exp Ther., 244(3):1157-1163, Mar. 1988.

Doose et al., "Severe Idiopathic Epilepsy of Infancy with Generalized Tonic-Clonic Seizures," Neuropediatrics, 29:229-38, Oct. 1998.

Dravet C. "Dravet syndrome history." Dev Med Child Neurol 2011 ;53 Suppl 2:1-6.

Dravet et al., "Severe Myoclonic Epilepsy in Infancy (Dravet syndrome)," In: Epileptic Syndromes in Infancy, Childhood and Adolescence. 4th ed., John Libbey Eurotext; 2005, pp. 89-113.

Duran, Marta et al. "Preliminary efficacy and safety of an oromucosal standardized cannabis extract in chemotherapy-induced nausea and vomiting : Standardized cannabis extract in chemotherapy-induced nausea and vomiting", British Journal of Clinical Pharmacology., vol. 70, No. 5, Jul. 12, 2010, pp. 656-663.

Elphick et al., "The Phylogenetic Distribution and Evolutionary Origins of Endocannabinoid Signaling," Handb Exp Pharmacol., (168):283-297, Feb. 2005.

Fenwick et al., "Cost-Effectiveness Acceptability Curves-Facts, Fallacies and Frequently Asked Questions," Health Econ., 13(5):405-415, May 2004.

Frame, D., "Best Practice Management of CINV in Oncology Patients: I. Physiology and Treatment of CINV," J. Support Oncol., 8(2 Suppl. 1):5-9, Mar.-Apr. 2010.

French et al., "The Influence of Formulation on Emission, Deaggregation and Deposition of Dry Powders for Inhalation," J Aerosol Sci., 27(5):769-783, Jul. 1996.

Freund et al., "Role of Endogenous Cannabinoids in Synaptic Signaling," Physiol. Rev., 83(3):1017-1066, Jul. 2003.

Gaoni et al., "Isolation, Structure, and Partial Synthesis of an Active Constituent of Hashish," J Am Chem Soc., 86(8):1646-1647, Apr. 1964.

Garrett et al., Pharmacokinetics of Δ9-tetrahydrocannabinol in Dogs. J Pharm Sci., 66(3):395-407, Mar. 1977.

Gebremedhin et al., "Cannabinoid CB1 Receptor of Cat Cerebral Arterial Muscle Functions to Inhibit L-type Ca2+ Channel Current," Am. J. Physiol., 276(6):H2085-H2093, Jun. 1999.

Gedde MM, Maa E. "Whole Cannabis Extract of High Concentration Cannabidiol may calm seizures in highly refractory pediatric patients." American Epilepsy Society Annual Meeting; Dec. 2013, 2 pgs.

Gilmore et al., "Antiemetic Guideline Consistency and Incidence of Chemotherapy-Induced Nausea and Vomiting in US Community Oncology Practice: Inspire Study," J Oncol. Pract., 10(1):68-74, Jan. 2014.

Gloss et al., "Cannabinoids for Epilepsy (Review)," Cochrane Database of Systematic Reviews, Issue 3, Art. CD009270, Mar. 2014, 25 pgs.

CANNABIDIOL-DOMINANT FORMULATIONS, METHODS OF MANUFACTURING, AND USES THEREOF

CROSS-REFERENCE TO RELATED APPLICATIONS

This application claims the benefit of U.S. Provisional Patent Application No. 63/181,955, filed on Apr. 29, 2021 and entitled Cannabidiol-Dominant Formulations, Methods of Manufacturing, and Uses Thereof. The entire contents of this patent application are expressly incorporated herein by reference.

TECHNICAL FIELD

This disclosure relates generally to cannabidiol formulations and to methods of manufacturing the same.

BACKGROUND

Cannabidiol (CBD) is a naturally occurring, non-psychotropic phytocannabinoid produced by *Cannabis sativa* L. CBD is presently marketed as an FDA- and EMA-approved drug for the treatment of epilepsy (Epidiolex®, GW Pharmaceuticals PLC). It is also used recreationally for a variety of ailments including pain, anxiety, and insomnia.

CBD exists as a white crystalline solid in its pure form with a melting point of 65-67° C. It is classified in the Biopharmaceutical Classification System (BCS) as a Class II drug due to its high intestinal permeability and low aqueous solubility. As demonstrated in several peer-reviewed academic studies, CBD generally exhibits low oral bioavailability in humans, which is attributed to its low aqueous solubility. This in turn leads to limited intestinal absorption, significant first-pass metabolism in the liver, and positive food-effect. Specialized formulations of CBD (e.g., self-emulsifying drug delivery systems [SEDDS], oil in water micro-/nano-emulsions) have demonstrated improvements in oral bioavailability by increasing aqueous solubility and mitigating the food-effect. However, significant first-pass metabolism remains a challenging barrier to overcome.

In both pharmaceutical and recreational contexts, CBD is commonly sold as purified botanical extract derived from hemp (*Cannabis sativa* L. with not more than 0.3% tetrahydrocannabinol [THC]) that is diluted in a carrier solvent such as medium-chain triglycerides or sesame oil (e.g., Epidiolee). The botanical extraction method and downstream purification method(s) vary considerably for commercially available CBD products leading to inconsistencies in reported biological effects. These inconsistencies may be attributed to the varying concentrations of THC, other phytocannabinoids, terpenes, and other natural products (e.g., flavonoids), all of which impart distinct pharmacological effects. Although this molecular complexity is potentially less suitable in pharmaceutical applications, there is increasing evidence that phytocannabinoids, terpenes, and flavonoids bind to a variety of biological receptors to impart superior pharmacological effects as compared to individual phytocannabinoids in isolation.

Administration of CBD by inhalation via vaporization with an electronic cigarette is one potential strategy to improve its bioavailability. Aqueous solubility, first-pass metabolism, and food-effect are significantly less important factors for pulmonary drug delivery because the drug directly enters systemic circulation after permeating the lung tissues and is, in part, distributed in the bloodstream to target organs and tissues prior to metabolism by the liver.

However, vaporization devices (e.g., electronic cigarettes) typically require the vaporizable components to be in liquid form to ensure proper functionality. Solid materials are generally considered incompatible with vaporization devices because they do not flow in the reservoir, which limits direct contact with the atomizer (containing a heating element and wicking material), thereby resulting in unsatisfactory vaporization. It is known to those skilled in the art that CBD may crystallize or precipitate as an amorphous solid after extraction from *Cannabis sativa* L. Post-extraction refinement (e.g., activated carbon filtration, distillation, chromatography) increases the purity of CBD in the botanical extract, which further promotes crystallization and/or precipitation. Thus, CBD in a native extract, distillate, or highly purified form is not suitable to be used directly in vaporization devices.

To address this issue, known techniques involve diluting CBD-dominant *cannabis* inputs with high concentrations of non-*cannabis*-derived components (e.g., propylene glycol, glycerol, polyethylene glycols, and exogenous terpenes). However, such methods are unsatisfactory because they contain components that may be harmful to human health when consumed by vaporization in such high concentrations. Further, many of these known formulations are not compatible with vaporization devices that require higher viscosity fluids.

SUMMARY

There remains a need for *cannabis*-derived liquid formulations that are stable, non-crystalline, and dominant in cannabidiol (CBD) that can perform exceptionally well for vaporization in electronic cigarettes without the use of potentially harmful additives.

In general, this disclosure relates to formulations and products derived from *Cannabis sativa* L. The resulting products comprise CBD as the primary phytocannabinoid, and further comprise additional phytocannabinoids including, but not limited to, THC, cannabigerol (CBG), cannabichromene (CBC), cannabinol (CBN), and/or cannabidivarin (CBDV). The additional phytocannabinoid(s) may be present in higher concentrations than what is typically observed in unrefined and refined *cannabis* extracts used in known formulations and may result in beneficial polypharmacological effects.

The present formulations can be manufactured by a sequential process of purification and removal of CBD from the material. In more detail, embodiments of the formulations can be manufactured by extracting *Cannabis sativa* L. plant matter using a solvent (e.g. ethanol or carbon dioxide), optionally followed by several refining steps, and then partially removing CBD through crystallization.

Embodiments of the present disclosure provide a number of advantages over conventional formulations. For example, the present formulations will not crystallize under a variety of storage and use conditions (e.g., across a temperature range of from about 22° C. to about −20° C. in both bulk storage and vaporizer cartridge form). Thus, the present formulations are suitable for use in vaporization devices (e.g., electronic cigarettes), which devices typically require formulations that remain in a non-crystalline, non-solid, or non-partially solid state. In further embodiments, as liquification of crystalline CBD requires relatively high temperatures, the present formulations can also be used in embodiments that include temperature-sensitive materials (e.g., terpenes).

In one example, a method of making a liquid cannabidiol-dominant formulation is described. The method includes extracting a *cannabis* extract from a *Cannabis sativa* L. plant matter, and optionally purifying the *cannabis* extract under a distillation process to provide a *cannabis* distillate. The method further includes a step of subjecting the *cannabis* extract and/or *cannabis* distillate to a crystallization process. The example specifies that the crystallization process includes heating and dissolving the *cannabis* extract and/or *cannabis* distillate in a non-polar hydrocarbon solvent to form a solution and subsequently cooling the solution in the presence of cannabidiol (CBD) seed crystal to induce nucleation to form solid CBD crystals. The CBD crystals are then removed from the solution to provide a resulting liquid cannabidiol-dominant formulation.

In another example, a liquid cannabidiol-dominant formulation is described. The liquid cannabidiol-dominant formulation comprises a primary phytocannabinoid comprising CBD, and one or more additional phytocannabinoids. The example specifies that the liquid cannabidiol-dominant formulation is formed by the process of the previous example.

In another example, a method of using a liquid cannabidiol-dominant formulation is described. The method includes providing a liquid cannabidiol-dominant formulation to a vaporization device. The example specifies that the liquid cannabidiol-dominant formulation is produced by a process including extracting a *cannabis* extract from a *Cannabis sativa* L. plant matter, and optionally purifying the *cannabis* extract under a distillation process to provide a *cannabis* distillate. The method further includes a step of subjecting the *cannabis* extract and/or *cannabis* distillate to a crystallization process. The example specifies that the crystallization process includes heating and dissolving the *cannabis* extract and/or *cannabis* distillate in a non-polar hydrocarbon solvent to form a solution and subsequently cooling the solution in the presence of cannabidiol (CBD) seed crystal to induce nucleation to form solid CBD crystals. The CBD crystals are then removed from the solution to provide the liquid cannabidiol-dominant formulation.

In another example, a vaporization system for oral inhalation is described. The vaporization system includes a vaporization device and a vaporizer cartridge containing a liquid cannabidiol-dominant formulation. The example specifies that the liquid cannabidiol-dominant formulation is produced by a process including extracting a *cannabis* extract from a *Cannabis sativa* L. plant matter, and optionally purifying the *cannabis* extract under a distillation process to provide a *cannabis* distillate. The method further includes a step of subjecting the *cannabis* extract and/or *cannabis* distillate to a crystallization process. The example specifies that the crystallization process includes heating and dissolving the *cannabis* extract and/or *cannabis* distillate in a non-polar hydrocarbon solvent to form a solution and subsequently cooling the solution in the presence of cannabidiol (CBD) seed crystal to induce nucleation to form solid CBD crystals. The CBD crystals are then removed from the solution to provide the liquid cannabidiol-dominant formulation. The cartridge containing the liquid cannabidiol-dominant formulation may be removable and/or replaceable from the vaporization device. The example further specifies that at least about 60% of the liquid cannabidiol-dominant formulation is consumed before reaching a vaporizer functionality endpoint of the vaporizer cartridge. Further, the cartridge may provide between about 100 and about 300 activations before reaching the vaporizer functionality endpoint of the vaporizer cartridge. Further, the liquid cannabidiol-dominant formulation may be combined with a *cannabis* extract, a *cannabis* distillate, CBD crystals, terpenes, or a combination thereof prior to using in the vaporization device.

While multiple embodiments are disclosed, still other features, objects, and advantages will become apparent from the description, figures, and from the claims. The figures and detailed description are to be regarded as illustrative in nature and not restrictive.

DETAILED DESCRIPTION

Figure 1:
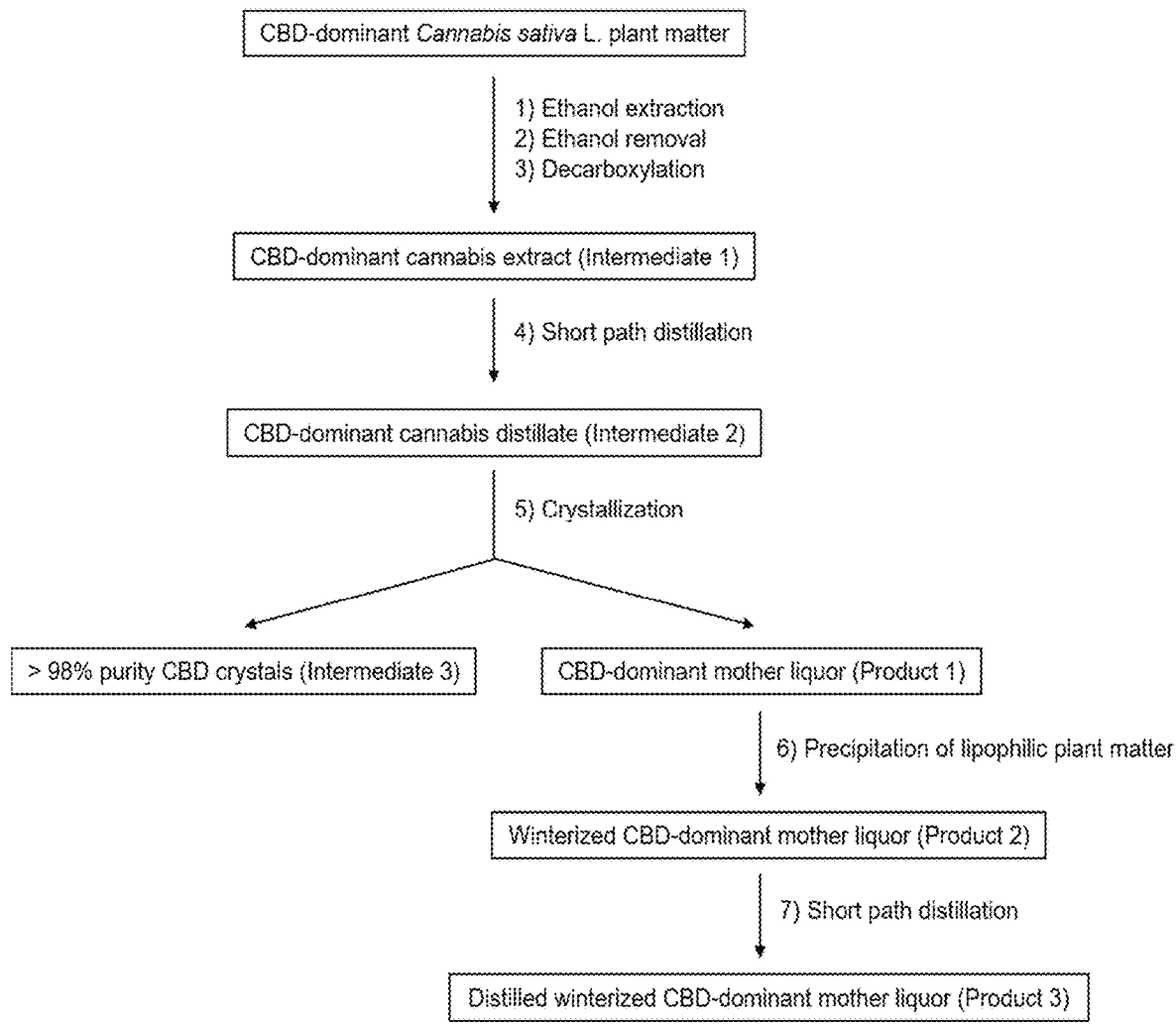
FIG. 1 is a flow chart of a manufacturing method in accordance with certain embodiments of the present disclosure.
Figure 2:
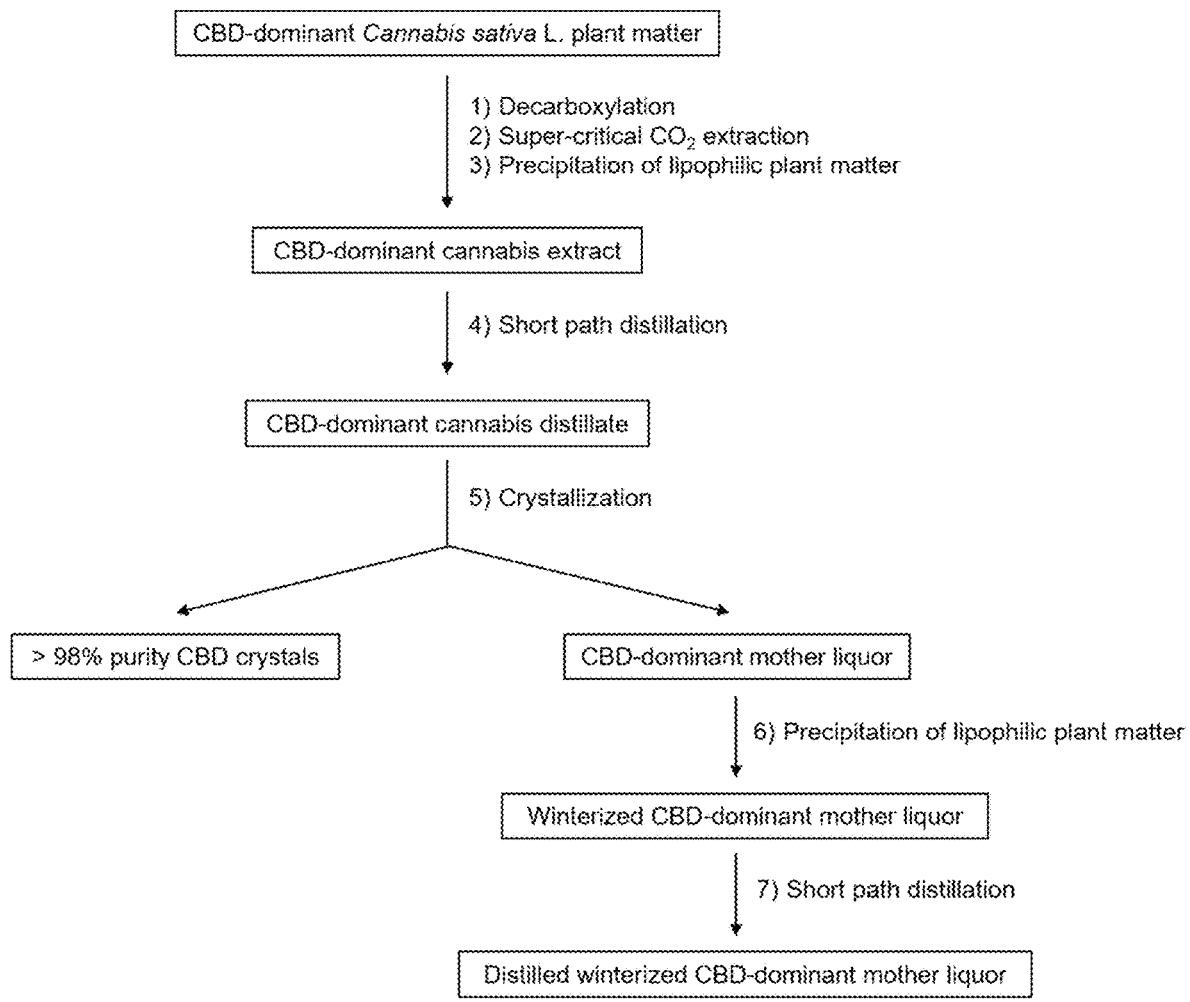
FIG. 2 is a flow chart of another manufacturing method in accordance with certain other embodiments of the present disclosure.

The following detailed description is to be read with reference to the drawings. The drawings depict selected embodiments and are not intended to limit the scope of the invention. Skilled artisans will recognize that the examples provided herein have many useful alternatives that fall within the scope of the disclosure.

As used herein, the term "about" modifying, for example, the quantity of an ingredient in a composition, concentration, and like values, and ranges thereof, employed in describing embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture.

The term "% w/w," "weight percent," "wt-%," "percent by weight," "% by weight," and variations thereof, as used herein, refer to the concentration of a substance as the weight of that substance divided by the total weight of the composition and multiplied by 100. It is understood that, as used herein, "percent," "%," and the like are intended to be synonymous with "weight percent," "% w/w," etc.

Numeric ranges recited within the specification are inclusive of the numbers defining the range and include each integer within the defined range. Throughout this disclosure, various aspects are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾%. This applies regardless of the breadth of the range.

The present disclosure relates generally to non-crystalline cannabidiol-dominant formulations in liquid form. Such formulations may be derived from *Cannabis sativa* L. In embodiments, the formulations are suitable for vaporization and manufactured by a process that provides for CBD and optionally other phytocannabinoids at higher concentrations than typically observed in unrefined and refined *cannabis* extracts. This may be the case for any embodiment of the present disclosure.

In certain embodiments, the input *cannabis* plant matter has a total CBD content (i.e., CBD % w/w+[0.877×cannabidiolic acid (CBDA) % w/w]) of from about 4% to about 30% w/w, from about 10% to about 30% w/w, from about 20% to about 30% w/w, or from about 25% to about 30% w/w. In some embodiments, the input *cannabis* plant matter has a total THC content (i.e., THC % w/w+[0.877×tetrahydrocannabinolic acid (THCA) % w/w]) of from 0% to about 5% w/w, from 0% to about 3% w/w, from 0% to about 2% w/w, from 0% to about 1% w/w, from about 0.5 w/w to about 5% w/w, from about 0.5% w/w to about 3% w/w, from about 0.5% w/w to about 2% w/w, from about 0.5% w/w to about 1% w/w, from about 0.1% w/w to about 5% w/w, from about 0.1 w/w to about 3% w/w, from about 0.1% w/w to about 2% w/w, or from about 0.1% w/w to about 1% w/w. In some cases, the input *cannabis* plant matter has a total CBD to total THC weight ratio of from about 5:1 to about 100:1, from about 10:1 to about 100:1, from about 25:1 to about 100:1, from about 40:1 to about 100:1, or from about 60:1 to about 100:1. In certain aspects, the input *cannabis* plant matter comprises *Cannabis sativa* L.

In certain embodiments, the *cannabis* oleoresin or *cannabis* extract is extracted using a solvent and through processes known to those skilled in the art. In aspects, the oleoresin or *cannabis* extract can be extracted from biomass with a wide variety of solvents including, but not limited to, ethyl alcohol, 2-propanol, supercritical $CO_2$, subcritical $CO_2$ (i.e., liquid $CO_2$), hexane, acetone, ethyl acetate, propane, butane, and any combination thereof. Suitable extraction conditions vary and are known to those skilled in the art. These include, but are not limited to, temperature, pressure, time, and solvent mixture ratios.

The *cannabis* oleoresin, and other extracts and/or distillates, may contain a significant amount of lipids and waxes depending on the conditions used during the extraction. *Cannabis* plants may contain a number of compounds, including plant waxes, fats, lipids, and chlorophyll, that need to be removed prior to further refinement. In certain embodiments, a process known as winterization, may optionally be used to remove these compounds and further refine the extract. In embodiments, this process involves the use of a solvent (e.g., ethyl alcohol, 2-propanol, or acetone) to dissolve the oleoresin, extract, and/or distillate, followed by a temperature shift down to about −20° C. to about −100° C., about −40° C. to about −90° C., or about −60° C. to about −90° C., for a sufficient period of time to precipitate the lipids and waxes from the mixture. In embodiments, the period of time to precipitate the lipids and waxes from the mixture may be in the range of from about 1 hour to about 24 hours, from about 5 hours to about 20 hours, or from about 10 hours to about 20 hours. These solids can then be removed by mechanical separation (e.g., filtration, centrifugation), and the solvent can then be removed using a thermal separation process (e.g., distillation) so as to provide a refined *cannabis* extract.

In certain embodiments, the refined *cannabis* extract may optionally be further purified using a distillation process (e.g., short path distillation) to provide a *cannabis* distillate. In certain aspects, the extract is heated under a vacuum such that desirable components evaporate and subsequently condense on a colder surface (i.e., condenser) so as to selectively separate the desirable components from the undesirable components. In embodiments, heating the extract under a vacuum separates impurities from the refined extract.

In certain embodiments, the *cannabis* extract and/or *cannabis* distillate is further refined using an adsorbent. The adsorbent may include, but is not limited to, activated carbon, silicon dioxide, magnesium silicate, alumina, acid-activated alumina, diatomaceous earth, bentonite clay, acid-activated bentonite clay, or a combination thereof. In some implementations, the *cannabis* extract and/or *cannabis* distillate is dissolved in a solvent that may include, but is not limited to, ethyl alcohol, 2-propanol, ethyl acetate, pentane, hexane, heptane, acetone, diethyl ether, methyl tert-butyl ether, or a combination thereof prior to processing with the adsorbent(s). This mixture can either be mixed with the adsorbent or passed over a column containing the adsorbent. Any adsorbent in the mixture can be removed by filtration and the solvent can be removed by subsequent distillation.

The *cannabis* extract and/or the *cannabis* distillate is subjected to a crystallization process to reduce the CBD concentration in the *cannabis* extract and/or *cannabis* distillate. This is in contrast to the purification processes listed above. Crystallization of CBD with CBD-rich starting material is disclosed. In some implementations of the crystallization process, the extract and/or distillate is heated and dissolved in a suitable non-polar hydrocarbon solvent to form a solution, and then cooled to a certain temperature at a certain rate in the presence of CBD seed crystal to nucleate the process of crystallization. In an aspect, the extract and/or distillate can be dissolved completely or partially within the suitable non-polar hydrocarbon solvent. In embodiments, the non-polar hydrocarbon may include n-pentane, n-hexane, n-heptane, n-octane, n-nonane, or a combination thereof. In further embodiments, the non-polar hydrocarbon comprises n-heptane. In embodiments, the temperature is cooled to a temperature of between about −10° C. and about 10° C., between about −5° C. and about 5° C., or between about −2° C. to about 2° C. In certain embodiments, the CBD seed crystal is highly concentrated, comprising greater than or equal to about 95% w/w of CBD, including greater than 96% w/w, and greater than 98% w/w of CBD. In certain embodiments, the CBD seed crystal is added to the solution prior to or concurrently with the cooling of the solution. In additional embodiments, the CBD seed crystal is added to the solution during the cooling of the solution once the temperature of the solution reaches between about 15° C. and about 35° C., between about 20° C. and about 30° C., or at about 25° C.

In aspects, the nucleation process forms solid CBD crystals within the solution. Once the nucleation process is complete, the CBD crystals can be removed by filtration. The remaining solution, termed mother liquor, can be converted to oil by removal of the hydrocarbon solvent (e.g., by distillation, evaporation, or other thermal separation process). The terms "mother liquor" and "liquid cannabidiol-dominant formulation" as used herein are intended to be synonymous and may be used interchangeably.

The processes above may be repeated on the mother liquor to further remove undesirable impurities. Specifically, winterization and distillation (e.g. short path distillation) processes may be repeated using the mother liquor instead of the *cannabis* oleoresin or *cannabis* extract as disclosed above. In embodiments, the winterization process comprises adding a solvent to the liquid cannabidiol-dominant formulation to form a solution, reducing the temperature of the solution to a range of between about −20° C. to about −100° C. to precipitate lipid solids from the solution, removing the lipid solids by filtration or centrifugation, and removing the solvent by distillation. In further embodiments, the distillation process comprises a short path distillation process comprising heating the liquid cannabidiol-dominant formulation under a vacuum to separate impurities from the liquid cannabidiol-dominant formulation.

The disclosure further provides for various methods of using a mother liquor or liquid cannabidiol-dominant formulation produced by the above processes. In certain embodiments, the mother liquor can be used after separating the CBD crystals from the mother liquor without any additional refining steps. In embodiments, the mother liquor is used directly in a vaporizer device. In certain embodiments, the mother liquor is winterized (e.g., according to the above-described procedure) prior to being used in a vaporizer device. In embodiments, the winterization process may optionally be accompanied by a heating step prior to shifting the temperature down to about −20° C. to about −100° C. In certain embodiments, the mother liquor is distilled prior to being used in a vaporizer device. In certain embodiments, the mother liquor is both winterized and distilled prior to being used in a vaporizer device.

In certain embodiments, the mother liquor, the winterized mother liquor, the distilled mother liquor, the distilled winterized mother liquor, or a combination thereof, is combined with *cannabis* extract, *cannabis* distillate, CBD crystals, terpenes, or a combination thereof prior to being used in a vaporizer device.

The formulations described in the present disclosure are intended for applications including, but not limited to, vaporization via electronic cigarette or other vaporization devices, smoking, liquid dosage forms for oral administration (such as oils, tinctures and beverages), and solid dosage forms. As used herein, tinctures and beverages include products described in the present disclosure that are diluted in carrier solvent(s) including, but not limited to, MCT oil, sesame oil, ethanol, canola oil, sunflower oil, palm kernel oil, monoglycerides, mono- and di-glycerides (e.g. glycerol monolinoleate), glycerol, propylene glycol, and water with or without surfactants and/or emulsifiers including, but not limited to, lecithins, polysorbates 20/60/80, vitamin E TPGS, Gelucire® 44/14, Kolliphor® EL, pectin, gelatin, maltodextrin, gum acacia, sucrose mono-, and/or di- and/or tri-esters of lauric, and/or palmitic and/or stearic acids, sucrose stearate, modified starches, carboxymethyl cellulose, carrageenan, guar gum, hydroxypropyl methylcellulose, tragacanth gum, xanthan gum, and sorbitan monostearate with or without natural and/or artificial flavors, and with or without natural and/or artificial sweeteners.

Solid dosage forms include, but are not limited to, orally disintegrating tablets, swallowable tablets, capsules, softgel capsules, confectionary such as chocolates, candy, and baked goods, and sublingual strips, (e.g., products described in this disclosure being diluted in an aforementioned carrier solvent(s) and incorporated into or onto a solid support or solid medium).

The disclosure further provides for cannabidiol-dominant formulations comprising CBD and one or more additional phytocannabinoids. In certain implementations, the formulations are formed by the processes described above to provide non-crystalline cannabidiol-dominant formulations.

In certain embodiments, the formulation comprises a primary phytocannabinoid comprising CBD, and one or more additional phytocannabinoids. In embodiments, the one or more additional phytocannabinoids comprises tetrahydrocannabinol (THC), cannabigerol (CBG), cannabichromene (CBC), cannabinol (CBN), cannabidivarin (CBDV), cannabidiolic acid (CBDA), tetrahydrocannabinolic acid (THCA), cannabigerolic acid (CBGA), cannabichromenic acid (CBCA), cannabinolic acid (CBNA), cannabidivarinic acid (CBDVA), or a combination thereof.

In certain embodiments, the concentration of CBD present in the formulation is from about 30% to about 70% w/w, from about 40% to about 70% w/w, from about 50% to about 70% w/w, or from about 60% to about 70% w/w. In certain embodiments, the concentration of THC present in the formulation is from 0% to about 10% w/w, from 0% to about 5% w/w, from about 0.5 w/w to about 10% w/w, from about 0.5% w/w to about 5% w/w, from about 0.1% w/w to about 10% w/w, or from about 0.1 w/w to about 5% w/w. In certain embodiments, the concentration of CBG present in the formulation is from 0% to about 10% w/w, or from 0% to about 5% w/w. In certain embodiments, the concentration of CBC present in the formulation is from about 1% to about 30% w/w, from about 5% to about 30% w/w, from about 1% to about 20% w/w, or from about 15% to about 30% w/w. In certain embodiments, the concentration of CBN present in the formulation is from 0% to about 30% w/w, from about 5% to about 30% w/w, from about 1% to about 15% w/w, or from about 15% to about 30% w/w. In certain embodiments, the concentration of CBDV present in the formulation is from 0% to about 10% w/w, or from 0% to about 5% w/w. In certain embodiments, the concentration of cannabidiolic acid (CBDA) present in the formulation is from 0% to about 5% w/w. In certain embodiments, the concentration of tetrahydrocannabinolic acid (THCA) present in the formulation is from 0% to about 5% w/w. In certain embodiments, the concentration of cannabigerolic acid (CBGA) present in the formulation is from 0% to about 5% w/w. In certain embodiments, the concentration of cannabichromenic acid (CBCA) present in the formulation is from 0% to about 5% w/w. In certain embodiments, the concentration of cannabinolic acid (CBNA) present in the formulation is from 0% to about 5% w/w. In certain embodiments, the concentration of cannabidivarinic acid (CBDVA) present in the formulation is from 0% to about 5% w/w.

In certain embodiments, the total terpene concentration present in the formulation is from 0% to about 15% w/w, from about 10% to about 15% w/w, from 0% to about 5% w/w, or from about 2% to about 10% w/w. As used herein, total terpene concentration is defined as the sum of the concentrations of α-Bisabolol, α-Cedrene, α-Humulene, α-Phellandrene, α-Pinene, α-Terpinene, α-Terpineol, β-Caryophyllene, β-Caryophyllene oxide, β-Myrcene, β-Ocimene, β-Pinene, Borneol, Camphene, Camphor, Cedrol, cis-Nerolidol, D-Limonene, $\Delta^3$-Carene, Eucalyptol, Fenchol, Fenchone, γ-Terpinene, Geraniol, Geranyl acetate, Guaiol, Isoborneol, Isopulegol, Linalool, Menthol, Nerol, p-Cymene, Phytol, Pulegone, Sabinene, Terpinolene, trans-Nerolidol, and Valencene. In certain embodiments, any one or more of these terpenes can be present in the formulation in an individual concentration of from 0% to about 5% w/w. In certain embodiments, the terpenes are derived from *Cannabis sativa* L. or other natural sources. In certain other embodiments, the terpenes are manufactured synthetically. In still other embodiments, the terpenes are derived from a combination of synthetic and natural sources.

In certain embodiments, the formulation contains less than 20% w/w of non-*cannabis* derived components such as propylene glycol, glycerol, polyethylene glycols, and exogenous terpenes. In additional embodiments, the formulation contains less than 15% w/w, less than 10% w/w, less than 5% w/w of the non-*cannabis* derived components. In further embodiments, the formulations may be substantially free (i.e., less than 0.5% w/w) of non-*cannabis* derived components such as propylene glycol, glycerol, polyethylene glycols, and exogenous terpenes.

In certain embodiments, the formulations are resistant to solidification and crystallization, demonstrating stability of the formulations. In embodiments, the formulations remain stable after a period of about 28 days when placed in storage conditions having a temperature of about 22° C. and about 40% relative humidity. In further embodiments, the formulations remain stable for a period of at least 7 days in storage conditions having a temperature of between about −20° C. to about 20° C.

Figure 3:
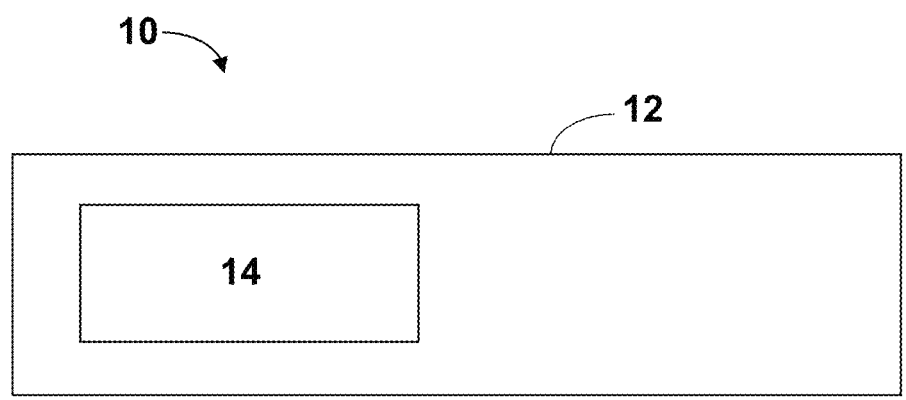
FIG. 3 is a schematic depiction of a vaporization system, including a vaporization device and a vaporization cartridge.

In an aspect, the formulations provide effective performance when used within a vaporization system. FIG. 3 depicts an implementation of a vaporization system. In embodiments, a vaporization system 10 includes a vaporization device 12 and a vaporization cartridge or reservoir 14. Vaporization device 12 may include a coil, a vaporization chamber, a battery, and a mouthpiece in addition to cartridge or reservoir 14. A wick may act as a bridge between the liquid in reservoir 14 and the vaporization chamber. In operation, the coil can heat the liquid to a specific temperature, e.g., releasing the active substance in the form of water vapor. For example, when a sensor inside the mouthpiece sense the inhalation via a change in pressure or otherwise by the user, the sensor may cause an atomizer to heat up. When the atomizer heats up it begins to heat the liquid from the reservoir. The substance vaped may be heated to a specific temperature (e.g., below that of combustion/smoke).

In some implementations, the vaporization cartridge 14 is permanently retained in the vaporization device 12, e.g., as a single use device. In other configurations, the vaporization cartridge 14 is removable and/or replaceable from the vaporization device 12. In either case, the vaporization cartridge 14 contains a liquid cannabidiol formulation. The liquid cannabidiol formulation can be the liquid cannabidiol-dominant formulation disclosed herein and/or as produced by the processes provided within this disclosure. The liquid cannabidiol formulation present in the vaporization cartridge 14 may or may not be admixed with additional constituent components.

In certain embodiments, the formulations of the disclosure may be used within the vaporizer cartridge. In aspects, the disclosed formulations can provide between about 100 and about 300 activations, between about 150 and about 250 activations, or between about 190 and 230 activations before reaching its vaporizer functionality endpoint. In aspects, the vaporizer functionality endpoint is the number of activations before the vaporizer cartridge weighs <5 mg per 10 activations (i.e., <0.5 mg *cannabis* oil inhaled per activation). In embodiments, at least about 50%, at least about 60%, at least about 70%, or at least about 75% of the formulation is consumed before reaching its vaporizer functionality endpoint. In further embodiments, the average quantity of vapor generated per activation is between about 1.5 mg and 3 mg, with the ability to reach a quantity of vapor generated of up to about 7 mg, about 6 mg, or about 5 mg per activation.

Products described in this disclosure can be used individually and/or in combination with other products and/or in combination with process intermediates and/or in combination with *cannabis*-derived terpenes and/or in combination with non-*cannabis*-derived terpenes.

EXAMPLES

Embodiments of the disclosure are further defined in the following non-limiting Examples. It should be understood that these Examples, while indicating certain embodiments, are given by way of illustration only. From the above discussion and these Examples, one skilled in the art can ascertain the essential characteristics of this disclosure, and without departing from the spirit and scope thereof, can make various changes and modifications of the embodiments to adapt it to various usages and conditions. Thus, various modifications of the embodiments, in addition to those shown and described herein, will be apparent to those skilled in the art from the foregoing description. Such modifications are also intended to fall within the scope of the appended claims.

Example 1—Manufacture of a Non-Crystalline Cannabidiol-Dominant Product

*Cannabis sativa* L. plant matter (REx™2000 micron, BC Hop Company Ltd.) was extracted with ethyl alcohol using a standard process known to those skilled in the art. Some of this material, termed Intermediate 1 (shown, for example, in FIG. 1), was distilled via short path wiped film distillation (Chemtech Services, Inc. KDT-6) using standard conditions known to those skilled in the art to yield intermediate 2 as a light yellow viscous semi-solid.

Intermediate 2 was subjected to a crystallization step to remove CBD from the mixture according to a standard process. The material was heated with n-heptane in a jacketed stirred tank reactor to create the crystallization solution. The solution temperature was decreased to 0° C. over 3 hours at a consistent rate and previously manufactured seed crystal (>99% CBD w/w) was added when the solution temperature reached 25° C. to induce nucleation. The crystal slurry was stirred for an additional hour after reaching 0° C. Separation of the solid CBD crystal (Intermediate 3) from the mother liquor (Product 1) was accomplished using a Buchner funnel. The CBD crystals were rinsed with n-heptane cooled to −20° C., and then dried to give Intermediate 1 as a white crystalline solid. The n-heptane was removed from the mother liquor in a solvent evaporation system at 80° C. and 5 mbar to yield Product 1 as a dark red viscous oil.

TABLE 1

Phytocannabinoid concentrations of process intermediates and final product described in Example 1 quantitated by HPLC-DAD using certified reference standards

| Cannabinoid | Intermediate 1 (% w/w) | Intermediate 2 (% w/w) | Intermediate 3 (% w/w) | Product 1 (% w/w) |
|---|---|---|---|---|
| CBD | 67.90 | 78.63 | 99.20 | 48.01 |
| CBDA | 0.28 | 0.29 | <0.01 | 0.78 |
| $\Delta^9$-THC | 2.03 | 2.00 | 0.04 | 5.15 |
| $\Delta^9$-THCA | <0.25 | <0.25 | <0.01 | <0.25 |
| CBN | <0.25 | 0.48 | 0.02 | 0.62 |
| CBNA | <0.25 | <0.25 | <0.01 | <0.25 |
| CBG | 1.18 | 1.20 | 0.03 | 2.92 |
| CBGA | <0.25 | <0.25 | <0.01 | <0.25 |

TABLE 1-continued

Phytocannabinoid concentrations of process intermediates
and final product described in Example 1 quantitated
by HPLC-DAD using certified reference standards

| Cannabinoid | Intermediate 1 (% w/w) | Intermediate 2 (% w/w) | Intermediate 3 (% w/w) | Product 1 (% w/w) |
|---|---|---|---|---|
| CBC | 3.03 | 4.40 | 0.01 | 7.95 |
| CBCA | <1.65 | <1.65 | <0.01 | <1.65 |
| CBDV | 0.24 | 0.73 | 0.25 | 1.66 |
| CBDVA | <0.25 | <0.25 | <0.01 | <0.25 |

Example 2—Winterization of a Non-Crystalline Cannabidiol-Dominant Product

Product 1 (mother liquor from Example 1) was heated to 80° C., added to ethyl alcohol (95% v/v, USP, Greenfield Global Inc.) and the mixture was stirred at 60° C. until Product 1 dissolved. The vessel was sealed and stored in a freezer at −80° C. for 15 hours. The resulting mixture was filtered using a Buchner funnel to remove residual lipophilic plant matter. The filtrate was transferred to a solvent evaporation system and the ethyl alcohol was removed at 80° C. and 5 mbar to yield Product 2 as a dark red viscous oil.

Example 3—Distillation of a Non-Crystalline Cannabidiol-Dominant Product

Product 2 (winterized mother liquor from Example 2) was distilled via short path wiped film distillation using standard conditions known to those skilled in the art to yield Product 3 as an amber viscous oil.

TABLE 2

Phytocannabinoid concentrations of Products 2 and 3 described
in in Examples 2 and 3, respectively, quantitated by
HPLC-DAD using certified reference standards

| Cannabinoid | Product 2 (% w/w) | Product 3 (% w/w) |
|---|---|---|
| CBD | 48.09 | 52.71 |
| CBDA | 0.69 | 0.79 |
| Δ$^9$-THC | 5.07 | 5.41 |
| Δ$^9$-THCA | <0.25 | <0.25 |
| CBN | 0.58 | 0.76 |
| CBNA | <0.25 | <0.25 |
| CBG | 2.80 | 3.07 |
| CBGA | <0.25 | <0.25 |
| CBC | 7.98 | 8.81 |
| CBCA | <1.65 | <1.65 |
| CBDV | 2.00 | 1.76 |
| CBDVA | <0.25 | <0.25 |

Example 4—Preparation of Vaporizer Cartridges Containing Cannabidiol-Dominant Intermediate 2

6 g of Intermediate 2 was heated at 80° C. until the CBD crystals melted and the resulting free-flowing liquid was transferred in equal proportions to 12×0.5 mL vaporizer cartridges (Jupiter, Liquid6™ ETP, 9W @ 3.5V, 510-thread connection, 2.0 mm inlet hole diameter). The cartridges were sealed with polycarbonate mouthpieces containing silicone seals and were stored vertically with the mouthpieces in an upward direction under ambient conditions (18-22° C., 20-40% relative humidity) for 7 days. 8 g of Intermediate 2 was stored in a 20 mL glass scintillation vial alongside the vaporizer cartridges.

Example 5—Preparation of Vaporizer Cartridges Containing Non-Crystalline Cannabidiol-Dominant Product 1

6 g of Product 1 was heated to 80° C. and transferred in equal proportions to 12×0.5 mL vaporizer cartridges (Jupiter, Liquid6™ ETP, 9W @ 3.5V, 510-thread connection, 2.0 mm inlet hole diameter). The cartridges were sealed with polycarbonate mouthpieces containing silicone seals and were stored vertically with the mouthpieces in an upward direction under ambient conditions (18-22° C., 20-40% relative humidity) for 7 days. 8 g of Product 1 was stored in a 20 mL glass scintillation vial alongside the vaporizer cartridges.

Example 6—Preparation of Vaporizer Cartridges Containing Non-Crystalline Cannabidiol-Dominant Product 3

6 g of Product 3 was heated to 80° C. and transferred in equal proportions to 12×0.5 mL vaporizer cartridges (Jupiter, Liquid6™ ETP, 9W @ 3.5V, 510-thread connection, 2.0 mm inlet hole diameter). The cartridges were sealed with polycarbonate mouthpieces containing silicone seals and were stored vertically with the mouthpieces in an upward direction under ambient conditions (18-22° C., 20-40% relative humidity) for 7 days. 8 g of Product 3 was stored in a 20 mL glass scintillation vial alongside the vaporizer cartridges.

Example 7—Preparation of a Cannabidiol-Dominant Formulation Containing Approximately 45% w/w CBD and 9% w/w Total Terpenes and Filling of Vaporizer Cartridges 14.25 g of Product 3 and 0.75 g of a plant-derived terpene blend (33.2% w/w D-Limonene, 26.1% w/w β-Caryophyllene, 12.7% w/w Linalool, 10.7% w/w β-Myrcene, 4.6% w/w α-Humulene, 3.3% w/w β-Pinene, 3.1% w/w trans-Nerolidol, 2.5% w/w α-Pinene, 1.2% w/w Geraniol, 1.2% w/w α-Terpineol, 0.8% w/w α-Phellandrene, 0.3% w/w α-Bisabolol, 0.2% w/w Guaiol, 0.2% w/w β-Caryophyllene oxide) were combined in a 20 mL scintillation vial. The vial was capped and heated to 80° C. The contents of the vial were mixed at 80° C. and 10,000 rpm for 2 minutes using a high shear homogenizer (Fisher Scientific™850 Homogenizer, 10×115 mm generator probe) to give Product 4 as an amber viscous liquid.

6 g of Product 4 was heated to 80° C. and transferred in equal proportions to 12×0.5 mL vaporizer cartridges (Jupiter, Liquid6™ ETP, 9W @ 3.5V, 510-thread connection, 2.0 mm inlet hole diameter). The cartridges were sealed with polycarbonate mouthpieces containing silicone seals and were stored vertically with the mouthpieces in an upward direction under ambient conditions (18-22° C., 20-40% relative humidity) for 7 days. 8 g of Product 4 was stored in a 20 mL glass scintillation vial alongside the vaporizer cartridges.

Example 8—Preparation of a Cannabidiol-Dominant Formulation Containing Approximately 50% w/w CBD and 9% w/w Total Terpenes and Filling of Vaporizer Cartridges 12.93 g of Product 3, 1.32 g of Intermediate 3 and 0.75 g of a plant-derived terpene blend (33.2% w/w D-Limonene, 26.1% w/w β-Caryophyllene, 12.7% w/w Linalool, 10.7% w/w β-Myrcene, 4.6% w/w α-Humulene, 3.3% w/w β-Pinene, 3.1% w/w trans-Nerolidol, 2.5% w/w α-Pinene, 1.2% w/w Geraniol, 1.2% w/w α-Terpineol, 0.8% w/w α-Phellandrene, 0.3% w/w α-Bisabolol, 0.2% w/w Guaiol, 0.2% w/w β-Caryophyllene oxide) were combined in a 20 mL scintillation vial. The vial was capped and heated to 80° C. The contents of the vial were mixed at 80° C. and 10,000 rpm for 2 minutes using a high shear homogenizer (Fisher Scientific™850 Homogenizer, 10×115 mm generator probe) to give Product 5 as an amber viscous liquid.

6 g of Product 5 was heated to 80° C. and transferred in equal proportions to 12×0.5 mL vaporizer cartridges (Jupiter, Liquid6™ ETP, 9W @ 3.5V, 510-thread connection, 2.0 mm inlet hole diameter). The cartridges were sealed with polycarbonate mouthpieces containing silicone seals and were stored vertically with the mouthpieces in an upward direction under ambient conditions (18-22° C., 20-40% relative humidity) for 7 days. 8 g of Product 5 was stored in a 20 mL glass scintillation vial alongside the vaporizer cartridges.

Example 9—Preparation of a Cannabidiol-Dominant Formulation Containing Approximately 55% w/w CBD and 9% w/w Total Terpenes and Filling of Vaporizer Cartridges 11.39 g of Product 3, 2.86 g of Intermediate 3 and 0.75 g of a plant-derived terpene blend (33.2% w/w D-Limonene, 26.1% w/w β-Caryophyllene, 12.7% w/w Linalool, 10.7% w/w β-Myrcene, 4.6% w/w α-Humulene, 3.3% w/w β-Pinene, 3.1% w/w trans-Nerolidol, 2.5% w/w α-Pinene, 1.2% w/w Geraniol, 1.2% w/w α-Terpineol, 0.8% w/w α-Phellandrene, 0.3% w/w α-isabolol, 0.2% w/w Guaiol, 0.2% w/w β-Caryophyllene oxide) were combined in a 20 mL scintillation vial. The vial was capped and heated to 80° C. The contents of the vial were mixed at 80° C. and 10,000 rpm for 2 minutes using a high shear homogenizer (Fisher Scientific™850 Homogenizer, 10×115 mm generator probe) to give Product 6 as an amber viscous liquid.

6 g of Product 6 was heated to 80° C. and transferred in equal proportions to 12×0.5 mL vaporizer cartridges (Jupiter, Liquid6™ ETP, 9W @ 3.5V, 510-thread connection, 2.0 mm inlet hole diameter). The cartridges were sealed with polycarbonate mouthpieces containing silicone seals and were stored vertically with the mouthpieces in an upward direction under ambient conditions (18-22° C., 20-40% relative humidity) for 7 days. 8 g of Product 6 was stored in a 20 mL glass scintillation vial alongside the vaporizer cartridges.

Example 10—Preparation of a Cannabidiol-Dominant Formulation Containing Approximately 60% w/w CBD and 9% w/w Total Terpenes and Filling of Vaporizer Cartridges 9.86 g of Product 3, 4.39 g of Intermediate 3 and 0.75 g of a plant-derived terpene blend (33.2% w/w D-Limonene, 26.1% w/w β-Caryophyllene, 12.7% w/w Linalool, 10.7% w/w β-Myrcene, 4.6% w/w α-Humulene, 3.3% w/w β-Pinene, 3.1% w/w trans-Nerolidol, 2.5% w/w α-Pinene, 1.2% w/w Geraniol, 1.2% w/w α-Terpineol, 0.8% w/w α-Phellandrene, 0.3% w/w α-Bisabolol, 0.2% w/w Guaiol, 0.2% w/w β-Caryophyllene oxide) were combined in a 20 mL scintillation vial. The vial was capped and heated to 80° C. The contents of the vial were mixed at 80° C. and 10,000 rpm for 2 minutes using a high shear homogenizer (Fisher Scientific™850 Homogenizer, 10×115 mm generator probe) to give Product 7 as an amber viscous liquid.

6 g of Product 7 was heated to 80° C. and transferred in equal proportions to 12×0.5 mL vaporizer cartridges (Jupiter, Liquid6™ ETP, 9W @ 3.5V, 510-thread connection, 2.0 mm inlet hole diameter). The cartridges were sealed with polycarbonate mouthpieces containing silicone seals and were stored vertically with the mouthpieces in an upward direction under ambient conditions (18-22° C., 20-40% relative humidity) for 7 days. 8 g of Product 7 was stored in a 20 mL glass scintillation vial alongside the vaporizer cartridges.

TABLE 3

Phytocannabinoid concentrations of Products 4-7 described in Examples 7-10 quantitated by HPLC-DAD using certified reference standards

| Cannabinoid | Product 4 (% w/w) | Product 5 (% w/w) | Product 6 (% w/w) | Product 7 (% w/w) |
|---|---|---|---|---|
| CBD | 49.85 | 53.84 | 58.69 | 62.87 |
| CBDA | 0.74 | 0.82 | 0.46 | 0.40 |
| Δ⁹-THC | 4.94 | 4.44 | 3.95 | 3.40 |
| Δ⁹-THCA | <0.25 | <0.25 | <0.25 | <0.25 |
| CBN | 0.82 | 0.76 | 0.68 | 0.60 |
| CBNA | <0.25 | <0.25 | <0.25 | <0.25 |
| CBG | 2.89 | 2.63 | 2.32 | 2.00 |
| CBGA | <0.25 | <0.25 | <0.25 | <0.25 |
| CBC | 8.29 | 7.53 | 6.66 | 5.76 |
| CBCA | <1.65 | <1.65 | <1.65 | <1.65 |
| CBDV | 1.63 | 1.50 | 1.35 | 1.21 |
| CBDVA | <0.25 | <0.25 | <0.25 | <0.25 |

TABLE 4

Terpene concentrations in the plant-derived terpene blend, Product 3 and Product 5 quantitated by GC-FID using certified reference standards

| Terpene | Plant-derived Terpene Blend (% w/w) | Product 3 (% w/w) no terpene blend added | Product 5 (% w/w) terpene blend added |
|---|---|---|---|
| D-Limonene | 33.18 | <0.005 | 1.78 |
| β-Caryophyllene | 26.14 | 0.05 | 1.48 |
| Linalool | 12.69 | <0.005 | 0.69 |
| β-Myrcene | 10.69 | <0.005 | 0.58 |
| α-Humulene | 4.61 | 0.05 | 0.30 |
| β-Pinene | 3.29 | <0.005 | 0.18 |
| trans-Nerolidol | 3.07 | 0.10 | 0.24 |
| α-Pinene | 2.54 | <0.005 | 0.13 |
| Geraniol | 1.17 | <0.005 | 0.06 |
| α-Terpineol | 1.22 | <0.005 | 0.07 |
| α-Phellandrene | 0.76 | <0.005 | <0.005 |
| α-Bisabolol | 0.28 | 2.89 | 2.21 |
| Guaiol | 0.18 | 0.44 | 0.37 |
| β-Caryophyllene oxide | 0.18 | 0.45 | 0.38 |
| Cedrol | <0.005 | 0.66 | 0.51 |
| Total | 100.00 | 4.65 | 8.97 |

Example 11—Stability of CBD-Dominant Intermediates and Products Described in this Disclosure at Varying Temperatures Using Resistance to Solidification and Crystallization as the Primary Indicator of Stability Twelve of the fifteen vaporizer cartridges and the bulk formulation samples described in Examples 4-10 (Intermediate 2, Product 1 and Products 3-7) were incubated in a stability chamber (Thermo Fisher Scientific, Environmental Chamber Model 3940) at 22° C. and 40% relative humidity for 28 days to assess resistance to solidification and crystallization. The vaporizer cartridges and bulk samples were removed from the stability chamber on day 29 and were visually inspected for signs of solidification and crystallization. The vaporizer cartridges and bulk samples were returned to the stability chamber and were incubated at 15° C. and 40% relative humidity for 7 days. Visual inspection was completed after 7 days (day 35). The vaporizer cartridges and bulk samples were returned to the stability chamber and were incubated at 5° C. and 40% relative humidity for 7 days. Visual assessment was completed after 7 days (day 42). The vaporizer cartridges and bulk formulations were then transferred to a freezer at −20° C. for 7 days. Visual inspection was completed after 7 days (day 49).

As shown in Table 5, Product 1 and Products 3-5 did not show any visible signs of solidification or crystallization in the vaporizer cartridges and bulk samples at any of the stability conditions tested. Product 7 and Intermediate 2 fully solidified and/or crystallized in 100% of the vape cartridges and bulk samples stored at 25° C. and 40% relative humidity for 28 days. Product 7 and Intermediate 2 were not subjected to the remainder of stability conditions (i.e., 15° C., 5° C. and −20° C.) because solidification and/or crystallization occurred at the "realistic use" conditions of 22° C. and 40% RH. Product 6 solidified and/or crystallized to varying degrees at the different stability conditions. Six of twelve vaporizer cartridges solidified and/or crystallized after 28 days at 22° C. and 40% RH. Two additional vaporizer cartridges solidified and/or crystallized after 7 days at 15° C. and 40% RH (8 of 12 vaporizer cartridges). One additional vaporizer cartridge solidified and/or crystallized after 7 days at 5° C. and 40% RH (9 of 12 vaporizer cartridges). No additional vaporizer cartridge solidified and/or crystallized after 7 days at −20° C. The bulk sample for Product 6 solidified and/or crystallized after 7 days at 15° C. and 40% RH.

TABLE 5

Stability results for Intermediate 2, Product 1 and Products 3-7

| Product # | Stability Conditions | Incubation Period | Observations |
|---|---|---|---|
| Products 1 and 3-5 | 22° C./40% RH | 28 days | No solidification or crystallization observed in vaporizer cartridges or bulk samples after the incubation periods for any of the stability conditions. |
| | 15° C./40% RH | 7 days | |
| | 5° C./40% RH | 7 days | |
| | −20° C. freezer | 7 days | |
| Product 6 | 22° C./40% RH | 28 days | Solidification and/or crystallization observed in 6 of 12 vaporizer cartridges |
| | 15° C./40% RH | 7 days | Solidification and/or crystallization observed in 8 of 12 vaporizer cartridges and the bulk sample. |
| | 5° C./40% RH | 7 days | Solidification and/or crystallization observed in 9 of 12 vaporizer cartridges |
| | −20° C. freezer | 7 days | Solidification and/or crystallization observed in 9 of 12 vaporizer cartridges |
| Product 7, Intermediate 2 | 22° C./40% RH | 28 days | Solidification and/or crystallization observed in 100% of vaporizer cartridges after 28 days at 25° C./40% RH. |
| | 15° C./40% RH | 7 days | |
| | 5° C./40% RH | 7 days | |
| | −20° C. freezer | 7 days | Vaporizers and bulk samples were not incubated at other stability conditions. |

Example 12—Performance of CBD-Dominant Intermediates and Products Described in the Disclosure in a Vaporization Machine Designed to Simulate Real World Vaporization Three of the fifteen vaporizer cartridges described in Examples 4, 5, 6 and 8 (i.e., Intermediate 2 and Products 1, 3, and 5) were incubated at 22° C. and 40% relative humidity in a stability chamber (Thermo Fisher Scientific, Environmental Chamber Model 3940) for 7 days. The vaporizer cartridges and bulk samples were removed from the stability chamber on day 8 and were visually inspected. All *cannabis* material in Intermediate 2 vaporizer cartridges fully solidified and/or crystallized after the 7 day stability period. No solidification or crystallization was observed in any of the vaporizer cartridges for Products 1, 3, or 5.

One vaporizer cartridge for each of Intermediate 2 and Products 1, 3, and 5 were connected to 510-thread batteries (Jupiter, 350 mAh lithium ion, 7.3W at 3.2V, inhalation activated) and were evaluated for performance using a simulated vaporizer machine (Gram Universal Vaping Machine, Inhalation Volume=60 mL, Inhale Duration=3 sec, Exhale Duration=5 sec, Rest Time Between Inhalations=30 sec). All vaporizer cartridges were weighed prior to the performance tests and every 10 activations thereafter. Testing was stopped when the difference in weight of the vaporizer cartridge was <5 mg per 10 activations, which indicates the endpoint of vaporizer functionality in real world scenarios (i.e., <0.5 mg *cannabis* oil inhaled per activation). The average quantity of vapor generated per activation and total *cannabis* oil utilization were calculated for the vaporizer lifecycle. The results were benchmarked to Intermediate 2, which is a vaporizer formulation commonly found in the North American *cannabis* markets. As shown in Table 6, Intermediate 2 reached its vaporizer functionality endpoint after 40 activations with only 11% of the *cannabis* oil consumed. Products 1, 3 and 5 reached their vaporizer functionality endpoints after 210, 230, and 190 activations, respectively, and consumed 75%, 86%, and 79% of the *cannabis* oil, respectively. The average quantity of vapor generated per activation was similar for all intermediates and products tested. The highest quantity of vapor generated per activation for Intermediate 2 and Products 1, 3, and 5 was 2.2 mg, 4.1 mg, 4.0 mg, and 3.6 mg, respectively. The results in Table 6 demonstrate that Products 1, 3, and 5 exhibit superior vaporizer performance compared to Intermediate 2 as measured by the total number of activations to vaporizer functionality endpoint, quantity of vapor produced per activation, and total *cannabis* oil utilization.

TABLE 6

Vaporizer cartridge performance data for representative examples of the disclosure

| Intermediate/Product # | Total Number of Activations to Endpoint | Average Vapor per Activation (mg) | | Total Cannabis Oil Utilization (%) |
|---|---|---|---|---|
| Intermediate 2 | 40 | High | 2.2 mg | 11% |
| | | Average | 1.4 mg | |
| | | Std Dev | ±0.6 mg | |
| | | RSD | 42% | |
| Product 1 | 210 | High | 4.1 mg | 75% |
| | | Average | 1.9 mg | |
| | | Std Dev | ±1.0 mg | |
| | | RSD | 50% | |
| Product 3 | 230 | High | 4.0 mg | 86% |
| | | Average | 2.0 mg | |
| | | Std Dev | ±1.1 mg | |
| | | RSD | 55% | |
| Product 5 | 190 | High | 3.6 mg | 79% |
| | | Average | 2.4 mg | |
| | | Std Dev | ±1.0 mg | |
| | | RSD | 42% | |

While some preferred embodiments of the invention have been described, it should be understood that various changes, adaptations, and modifications may be made therein without departing from the spirit of the invention.

The invention claimed is:

1. A method of making an oil cannabidiol dominant formulation, comprising:
   a. extracting *Cannabis sativa* to form a *Cannabis sativa* extract;
   b. purifying the *Cannabis sativa* extract via a distillation process to yield a *cannabis* distillate;
   c. heating and dissolving the *cannabis* distillate in a non-polar hydrocarbon solvent to form a solution;
   d. combining the solution with previously manufactured cannabidiol seed crystals to induce nucleation to form solid cannabidiol crystals;
   e. removing the solid cannabidiol crystals from the solution to yield a liquid cannabidiol-dominant formulation; and
   f. removing the non-polar hydrocarbon solvent from the liquid cannabidiol-dominant formulation to yield an oil cannabidiol dominant formulation.

2. The method of claim 1, wherein the *Cannabis sativa* L. has a total CBD content of from about 4% to about 30% w/w, a total THC content of from 0% to about 5% w/w, or a total CBD to total THC weight ratio of from about 5:1 to about 100:1.

3. The method of claim 1, wherein the *cannabis* extract is extracted from the *Cannabis sativa* L. plant matter using a solvent selected from the group consisting of ethanol, 2-propanol, supercritical CO2, subcritical CO2, hexane, acetone, ethyl acetate, propane, butane, and combinations thereof.

4. The method of claim 1, wherein the solution is cooled to a temperature of between about −10° C. and about 10° C. during the crystallization process, and wherein the CBD seed crystal comprises greater than or equal to 95% w/w of CBD.

5. The method of claim 1, wherein the CBD seed crystal is added to the solution prior to, or concurrently with the cooling, or wherein the CBD seed crystal is added to the solution at a temperature of between about 20° C. and 30° C. during the cooling of the solution.

6. The method of claim 1, wherein the method further comprises a step of subjecting the liquid cannabidiol-dominant formulation to a winterization process, a second distillation process, or a combination thereof.

7. The method of claim 6, wherein the winterization process comprises adding a solvent to the liquid cannabidiol-dominant formulation to form a solution, reducing the temperature of the solution to a range of between about −20° C. to about −100° C. to precipitate lipid solids from the solution, removing the lipid solids by filtration and/or centrifugation, and removing the solvent by distillation.

8. The method of claim 6, wherein the second distillation process comprises a short path distillation process comprising heating the liquid cannabidiol-dominant formulation under a vacuum to separate impurities from the liquid cannabidiol-dominant formulation.

\* \* \* \* \*